(12) United States Patent
Wolfe et al.

(10) Patent No.: US 7,402,308 B1
(45) Date of Patent: Jul. 22, 2008

(54) METHOD OF DELIVERING GENES TO THE CENTRAL NERVOUS SYSTEM OF A MAMMAL

(75) Inventors: John H. Wolfe, Philadelphia, PA (US); Nigel W. Fraser, Philadelphia, PA (US)

(73) Assignees: Trustees of the University of Pennsylvania, Philadelphia, PA (US); The Wistar Institute, Philadelphia, PA (US)

( * ) Notice: Subject to any disclaimer, the term of this patent is extended or adjusted under 35 U.S.C. 154(b) by 0 days.

(21) Appl. No.: 08/393,066

(22) Filed: Feb. 23, 1995

Related U.S. Application Data (63) Continuation-in-part of application No. 08/020,177, filed on Feb. 22, 1993, now abandoned, which is a continuation of application No. 07/676,894, filed on Mar. 28, 1991, now abandoned.

(51) Int. Cl.
*A01N 63/00* (2006.01)
*A61K 48/00* (2006.01)
*C12N 15/00* (2006.01)

(52) U.S. Cl. .................. 424/93.21; 435/320.1
(58) Field of Classification Search .............. 514/44; 424/93.2, 93.21; 435/320.1
See application file for complete search history.

(56) References Cited

U.S. PATENT DOCUMENTS 5,849,572 A * 12/1998 Glorioso .................. 435/320.1

OTHER PUBLICATIONS

Nishimura et al (1986) Proced. Natl. Acad. Sci. 83, 7292-7296.*
Fink et al. Advances in the Developmental of Herpes Simplex Virus-Based Gene Transfer Vectors of the Nervous System. Clinical Neuroscience. vol. 3, 1996, pp. 284-291.*
Blomer et al. Applications of Gene Therapy to the CNS. Human Molecular Genetics. vol. 5 Review, 1996, pp. 1397-1404.*
Eck et al. Gene Based Therapy in The Pharmacological Basis of Therapeutics, Goodman and Gillman, eds. 9th edition, McGraw-Hill New York, 1996, 77-101.*
Wolfe et al. Herpesvirus Vector Gene Transfer and Expression of B-Glucuronidase in the Central Nervous System of MPS VII Mice. Nature Genetics. vol. 1, Aug. 1992, pp. 379-384.*
Palella et al. Expression of Human HPRT mRNA in Brains of Mice Infected with a Recombinant Herpes Simplex Virus-1 Vector. Gene, vol. 80, 1989, pp. 137-144.*
Dobson et al. Identification of the Latency-Associated Transcript Promoter by Expression of Rabbit Beta-Globin mRNA in Mouse Sensory Nerve Ganglia Latently Infected with a Recombinant Herpes Simplex Virus. J. Virology, vol. 63, 1989, pp. 3844-3851.*
Nishimura et al. Nucleotide Sequence of Rat Preputial Glan B-Glucuronidase cDNA and In Vitro Insertion of its Encoded Polypeptide into Microsomal Membranes. Proced. Natl. Acad. Sci. USA, vol. 83, Oct. 1986, pp. 7292-7296.*

Blau et al. Molecular Medicine: Gene Therapy—A Novel From of Drug Delivery, The New England Journal of Medicine. Nov. 2, 1995, pp. 1204-1207.*
Verma et al. Gene Therapy—Promises, Problems and Prospects. Nature, vol. 389, Sep. 18, 1997, pp. 239-242.*
Gene Therapy's Growing Pains. Science. vol. 269, Aug. 25, 1995, pp. 1050-1055.*
Anderson. Gene Therapy. Scientific American. Sep. 1995, pp. 124-126 and 128.*
Guise et al. Isolation and Expression in *Escherichia coli* of a cDNA Clone Encoding Human Beta-Glucuronidase. Gene. 1985, vol. 34, pp. 1-5-110.*
Steiner et al., "A herpes simplex virus type 1 mutant containing a non-transinducing Vmw65 protein establishes latent infection in mouse trigeminal ganglia in the absence of viral replication", *J Virol*, 64:1630-1638 (1990).
Steiner et al., "Herpes simplex virus type 1 latency-associated transcripts are not essential for latent infection," EMBO 8:505-511 (1989).
Stevens et al., "RNA complementary to a herpesvirus a gene mRNA is prominent in latently infected neurons," Science 235:1056-1969 (1987).
Tenser, et al., "Latency-associated transcript but not reactivatable virus is present in sensory ganglion neurons after inoculation of thymidine kinase-negative mutants of herpes simplex virus type 1," J. Virol. 63:2861-2865 (1989).
Ugolini et al., "Transneuronal transfer of herpes virus from peripheral nerves to cortex and brainstem", *Science* 243:89-91 (1989).
Villarreal et al., "Hybridization in situ of SV40 plaques: detection of recombinant SV40 virus carrying specific sequences of nonviral DNA," Science 196:183-185 (1977).
Vogler et al., "A murine model of mucopolysaccharidosis VII. Gross and microscopic findings in beta-glucuronidase-deficient mice", Am. J. Pathol., 136:207-217 (1990).
Wechsler et al., J Virol. 62:4051-58 (1988).
Wolfe, et al., "Restoration of normal lysosomal function in mucopolysaccharidosis type VII cells by retroviral vector-mediated gene transfer," Proc. Natl. Acad. Sci. 87:2877-2881 (1990).
Card et al., "Neurotropic properties of pseudorables virus: uptake and transneuronal passage in the rat central nervous system", *J. Neurosci.*, 10:1974-1994 (1990).
Deiss et al., "The herpes simplex amplicon: cleavage of concatemeric DNA is linked to packaging and involves the amplification of the terminally reiterated a sequence," *J. Virol.* 57:933-941 (1986).
Dobson et al., "Identification of the latency-associated transcript promoter by expression of rabbit β-globin mRNA in mouse sensory nerve ganglia latently infected with a recombinant herpes simplex virus", J Virology, vol. 63, No. 9, pp. 3844-3851 (1989).

(Continued)

*Primary Examiner*—Deborah Crouch
(74) *Attorney, Agent, or Firm*—Licata & Tyrrell PC (57) ABSTRACT

The invention provides a method of delivering a selected DNA sequence to the central nervous system of a mammal by administering to said mammal a neurotropic virus, said virus containing a selected DNA sequence under the control of a promoter which permits expression of the DNA during the latent infectious state of the virus.

8 Claims, 3 Drawing Sheets

OTHER PUBLICATIONS

Fraser et al., "Molecular biology of latent HSV-1, In: Human herpes virus infections. II viral glycoproteins and immunobiology", Raven Press NY 39-55 (1986).

Friedmann, T., "Progress toward human gene therapy", *Science* 244:1275-1281 (1989).

Geller, A.I., Breakfield, X.O., "A defective HSV-1 vector expresses *Escherichia coli* β-galactosidase in cultured peripheral neurons", Science, 241:1667-69 (Sep. 23, 1988).

Geller, A.I., Freese, A., "Infection of cultured central nervous system neurons with a defective herpes simplex virus 1 vector results in stable expression of *Escherichia coli* β-galactosidase", Proc Natl Acad Sci, 87:1149-1153 (1990).

Goldstein et al., "An ICP6::lacZ insertion mutagen is used to demonstrate that the UL52 gene of herpes simplex virus type 1 is required for virus growth and DNA synthesis," J. Virol. 62:2970-2977 (1988).

Ho et al., "β-galactosidase as a marker in the peripheral and neural tissues of the herpes simplex virus-infected mouse," Virology 167: 279-283 (1988).

Ho et al., "Herpes simplex virus latent RNA (LAT) is not required for latent infection in the mouse," Proc. Natl. Acad. Sci. USA 86:7596-7600.

Hoogerbrugge et al., "Donor-derived cells in the central nervous system of twitcher mice after bone marrow transplantation", *Science* 239:1035-1038 (1988).

Leib et al., "A deletion mutant of the latency-associated transcript of herpes simplex virus type 1 reactivates from the latent state with reduced frequency," J. Virol. 63:2893-2900 (1989).

McGeoch et al., Gen Virol, 69:1531-4 (1988).

Pallela et al., "Expression of human HPRT in mRNA in brains of mice infected with a recombinant herpes simplex virus-1 vector", *Gene*, 80:137-44 (1989).

Pallela et al., "Herpes simplex virus-mediated human hypoxanthine-guanine phosphoribosyltransferase gene transfer into neuronal cells", Molecular and Cellular Biology, vol. 8, No. 1 pp. 457-460 (1988).

Perry et al., J Gen Virol. 69:2931-46 (1988).

Spaete et al., "The herpes simplex virus amplicon: a new eucaryotic defective-virus cloning-amplifying vector," Cell 30:295-304 (1982).

Spivack et al., "Detection of herpes simplex virus type 1 transcripts during a latent infection in mice," J. Virol. 61:3841-3847 (1987).

* cited by examiner

Fig. 1

METHOD OF DELIVERING GENES TO THE CENTRAL NERVOUS SYSTEM OF A MAMMAL

INTRODUCTION

This application is a continuation-in-part application of U.S. Ser. No. 08/020,177 filed Feb. 22, 1993, now abandoned which is a continuation application of U.S. Ser. No. 07/676,894 filed Mar. 28, 1991 now abandoned. This invention was made in the course of research sponsored by the National Institutes of Health. The U.S. Government may have certain rights in this invention.

FIELD OF THE INVENTION

This invention relates to the field of mammalian somatic cell gene transfer. More particularly, methods are provided of delivering foreign genes to the central nervous system (CNS) of a mammal by administering to a mammal a recombinant neurotropic virus capable of expressing the foreign gene in the CNS of the mammal.

BACKGROUND OF THE INVENTION

A large number of the human genetic diseases result from deficiencies of enzyme activity in metabolic pathways. Some of the enzyme deficiency diseases can be ameliorated by dietary restriction, enzyme replacement, or enzyme manipulation, but this approach has only limited applications. Allotransplantation of tissues from a genetically normal donor into a patient to provide a source of normal enzyme has produced encouraging results in a small number of animal and human patients. However, this approach is limited by the frequent lack of a histocompatible donor, and by the relatively high morbidity and mortality of the procedure even when a matched donor is available. Somatic cell gene therapy has the potential to overcome these limitations by transferring a normal copy of a defective gene into a patient's own cells and returning the corrected cells to the patient's body by autologous transplantation.

The objective of gene therapy is to permanently correct the genetic defect in the target cells. Although showing great promise, gene therapy has encountered a number of difficulties.

The gene involved in the disease must be identified and cloned. Although self-apparent, this has not been accomplished for many genetic diseases. At the present time, the lack of cloned genes precludes the use of many animal models of human genetic disease for gene therapy studies.

A vector system must be developed that is capable of stably transferring the gene into the appropriate target cell. Several methods have been developed to transfer cloned genes into mammalian cells, achieve stable integration into the host cell DNA, and express the transferred gene. The most widely used method for gene therapy studies is the replication-defective retroviral vector system, which can transfer genes into a high percentage of target cells in tissue culture. However, the types of cells and, consequently, the diseases that are candidates for gene therapy using this method are limited by the fact that target cells must undergo mitosis for vector provirus integration to occur.

The transferred gene must be appropriately expressed in the diseased target cells. A major problem encountered in retroviral vector gene transfer into somatic cells, particularly bone marrow cells, has been that the expression of the inserted gene is either abrogated or substantially reduced when the cells containing the transferred gene are returned to the animal host. The failure of transduced hematopoietic cells to maintain expression of a vector gene in vivo may be caused by vector dysfunction, poor survival of the transfected cells, selection against the transfected cells by the host, or low efficiency of transfer into true pluripotent hematopoietic stem cells. Inadequate expression of the transferred gene in vivo may also be a consequence of not including all of the necessary regulatory elements in the vector design. To overcome this obstacle, new vectors have achieved improved expression by using internal promoters to regulate expression, by including certain intronic genomic sequences and, in the double-copy (DC) vectors, by moving the transferred gene outside the retroviral transcription unit. The correctly expressed transferred gene must be able to cure or significantly alter the course of the disease. A crucial test of the feasibility of applying gene therapy methods to human patients will be the demonstration of its effectiveness in altering the pathophysiology of disease in animal models. Progress in gene therapy has been hampered because animal disease models have not yet been discovered or created for most of the human genetic diseases in which the cloned gene is available.

The pluripotent hematopoietic stem cell is a major target for either replacement by transplanted normal allogeneic cells or correction by gene transfer in disorders such as lysosomal storage diseases. The basis for this approach is that lysosomal enzymes can be exported from normal to mutant cells via both receptor-mediated endocytosis and direct intercellular transfer of the enzyme. Bone marrow transplantation studies indicate that circulating blood cells producing normal lysosomal enzymes can export the enzyme to other cell types in sufficient amounts to impede or reverse the storage process in certain tissues. Thus, sustained expression of a vector-transferred lysosomal enzyme gene in autologously transplanted hematopoietic cells, when achievable, may be an effective approach to therapy for some organ systems. However, bone marrow transplantation has not been very effective in lysosomal storage diseases.

Treating the CNS disease will be critical in human patients with disorders of the CNS such as lysosomal storage diseases because many are mentally retarded and may benefit from such treatment. Whether enzymes can be exported to the CNS from donor bone marrow-derived cells has been a difficult problem to address experimentally because most studies have been performed in limited numbers of human patients or outbred domestic animals. Nevertheless, widespread increase of fucosidase enzyme activity in leukocytes, plasma, and visceral tissues was accompanied by a rapid improvement in the peripheral nerve and visceral lesions of fucosidosis and more gradual improvement in the CNS after bone marrow reconstitution in dogs with $\beta$-fucosidase deficiency and $\alpha$-L-iduronidase deficiency. Also, post-transplantation improvements in mental development have been reported in a child with MPS IH and a child with aryl sulfatase-A deficiency. In contrast, in other lysosomal storage diseases little evidence has been found for alteration of the CNS in post-transplant animals. For example, in both Niemann-Pick mice (spm/spm) and MPS VII mice, bone marrow transplantation resulted in increased levels of activity of the missing enzyme and marked improvement in many affected organs such as spleen and liver, but neurological manifestations were not improved, nor was enzyme activity significantly increased in the CNS.

The failure of bone marrow transplantation to affect the CNS may be due to the inability of either hematopoietic cells or exported enzyme to cross the blood-brain barrier. Some experiments suggest that disruption of this barrier may allow some cells or enzyme to enter the CNS. In preliminary studies in MPS VII mice, increasing the dose of radiation to recipient mice resulted in a small increase in the level of β-gus activity in the CNS of long-term chimeras. The infiltration of donor-derived enzymatically competent, foamy macrophages in the CNS of bone marrow transplanted recipients has been shown in "twitcher" mice [Hoogerbrugge et al., "Donor-derived cells in the central nervous system of twitcher mice after bone marrow transplantation", *Science* 239:1035-1038 (1988)]. However, it is not known whether the presence of donor cells in the CNS is due to normal migration of the cells or if normal barriers to such migration have been disrupted by the disease process, in which toxic amounts of psychosine accumulate intercellularly in the CNS as a result of the defect in galactosylceramidase. In addition, even with appropriate allotransplantation, a major complication is fatal sepsis resulting from the immunosuppressive drugs administered to prevent graft rejection.

New approaches are needed to achieve significant alterations in the CNS component of disorders of the CNS. One approach for delivering gene products to the CNS is to engraft genetically altered cells into the brain as a source of a biological molecules [T. Friedmann, "Progress toward human gene therapy", *Science* 244:1275-1281 (1989)]. This approach has been used to introduce nerve growth factor (NGF) into rat brains by transplantation of fibroblasts expressing a retroviral vector transferred NGF cDNA. A second approach to delivering gene products to the CNS is using neurotropic viruses as vectors to transfer the gene into CNS cells.

Infection with herpes simplex virus (HSV-1), a neurotropic virus, begins with viral replication in epithelial tissues. After initial replication at the site of infection, HSV-1 establishes latent infection in the nervous system during which no virus can be detected unless reactivation occurs. However, during latency viral DNA can be detected in the CNS of mice and humans [Fraser et al., "Molecular biology of latent HSV-1. In: Human herpes virus infections. II viral glycoproteins and immunobiology", Raven Press NY 39-55 (1986)]. Latent HSV-1 can be found in more than 80% of humans of which 30% have occasional reactivations in the form of cold sores.

Latency is established in the neuron and the establishment of latency probably depends on the lack of specific factors or specific interactions of the virus with the neuron. Estimates of the proportion of latently infected cells in sensory ganglia are in the range of 0.1-1%, based on reactivation from dissociated cell preparations. It has been suggested that specific viral gene products may be required for the establishment of a latent infection. However, results from experiments using HSV-1 temperature-sensitive mutants (both DNA replication positive and negative) suggest that neither DNA replication nor a productive infection are absolute requirements for establishing a latent infection. Furthermore, recent results suggest that no viral gene product is required for latency.

The acute viral infection is cleared by the immune system but there is little convincing evidence that clearly implicates involvement of the immune system in establishment, maintenance or reactivation of latency.

Using in situ hybridization and Northern blotting, the viral transcripts expressed during latency have been mapped to one small region of the viral genome—the repeat long region. These results in animal models have been repeated with human tissue. The transcripts made during latency have been called latency-associated transcripts (LATs) and their promoter has been mapped to a specific TATAA box within the repeat long region of the viral genome. LAT RNAs do not have an essential role in latency but they may play a role in the efficiency or speed of reactivation of the virus. Data suggest that the lytic and latent viral cycles are separate and that it is the absence of the virion-encoded transactivating factor which causes a latent infection to be established.

The LAT gene product has been seen to accumulate to high levels in the neuronal cells of both latently infected animals and humans for the life of the animal. All other HSV-1 genes are silent during latency. Thus it has been thought that the promoter of the LAT gene could be used to express foreign genes during latency. One group has constructed a virus containing the β-globin gene inserted 26 bases downstream of the TATA box of the LAT promoter and documented expression of the reporter gene in the peripheral nervous system for up to three weeks after establishment of the latency [Dobson et al., "Identification of the latency-associated transcript promoter by expression of rabbit β-globin mRNA in mouse sensory nerve ganglia latently infected with a recombinant herpes simplex virus", *J Virology*, vol. 63, No. 9, pp 3844-51 (1989)]. Their analysis of RNA indicated that appropriate splicing, polyadenylation and cytoplasmic transport of the β-globin gene occurred in the spinal ganglia indicating that the neurons of the peripheral nervous system have appropriate transcription and translation machinery. Another group tested a recombinant HSV-1 vector wherein the β-galactosidase gene was placed about 823 base pairs (bp) downstream of the LAT promoter [Ho et al., "Herpes simplex virus latent RNA (LAT) is not required for latent infection in the mouse," *Proc. Natl. Acad. Sci. USA* 86:7596-7600 (1989)]. Although the viruses expressed foreign genes during latency in vivo, the documented expression was limited to the peripheral nervous system. Id. Recombinant HSV-1 vectors also have been constructed using the HSV-1 immediated early (IE 4/5) or TK promoters to express the β-galactosidase or HPRT genes [Pallela et al., "Expression of human HPRT in mRNA in brains of mice infected with a recombinant herpes simplex virus-1 vector", *Gene*, 80:137-44 (1989); Pallela et al., "Herpes simplex virus-mediated human hypoxanthine-guanine phosphoribosyltransferase gene transfer into neuronal cells", *Molecular and Cellular Biology*, vol. 8, No. 1 pp 457-60 (1988); Geller, A. I., Breakfield, X. O. "A defective HSV-1 vector expresses *Escherichia coli* β-galactosidase in cultured peripheral neurons", *Science,* 241:1667-69 (23 Sep. 1988); Geller, A. I., Freese, A., "Infection of cultured central nervous system neurons with a defective herpes simplex virus 1 vector results in stable expression of *Escherichia coli* β-galactosidase", *Proc Natl Acad Sci,* 87:1149-1153 (1990) and Ho et al., "β-galactosidase as a marker in the peripheral and neural tissues of the herpes simplex virus-infected mouse," *Virology* 167: 279-283 (1988)].

There exists a need for vectors which can deliver foreign genes to, and express them in, the central nervous system preferably on a long term basis in order to modulate biological properties of the central nervous system, such as are found in disease states affecting the central nervous system.

SUMMARY OF THE INVENTION

An object of the present invention is to provide a method of delivering a gene or selected DNA sequence to the central nervous system of a mammal which comprises administering to said mammal a neurotropic virus, said virus containing a selected DNA sequence under the control of a promoter which permits expression of the gene during the latent infectious state of the virus.

The ability to introduce a gene into the mammalian central nervous system in vivo, thereby altering the physiology of the CNS, is an important advance in the field of neurobiology, and in gene therapy for genetic diseases leading to neurological disorders. In this area, neurotropic viruses such as HSV-1 are useful vector systems possessing a number of attractive features. These include, for example, the ability to deliver a gene directly into post mitotic cells; a wide host range; and maintenance indefinitely in a latent state in postmitotic neuronal cells.

BRIEF DESCRIPTION OF THE DRAWINGS

FIG. 1. Map of HSV-1 genome. Restriction enzyme cut sites, and other map positions are according to Perry et al., *J Gen Virol*, 69:2931-46 (1988)). A) Genome consists of a long unique ($U_L$) and short unique ($U_S$) region bounded by terminal ($TR_L$ and $TR_S$) and internal repeats ($IR_L$ and $IR_S$). B) BamHI fragments positive by in situ hybridization for latency associated transcripts are shaded. C) BamHI B and BamHI E both contain a 6.7 kb part derived from the long repeat region. Viral genes being transcribed from BamHI E and B are illustrated.

FIG. 2. Useful restriction sites and the LAT coding region within the BamHI E fragment of HSV-1 is show. A TATA box (inverted triangle) is located 686 nucleotides upstream from the transcriptional start site; a CAAT box (filled circle) is located 817 nucleotides upstream, three Sp1 binding sites (filled squares) are at 886, 862, and 589 nucleotides upstream. All promoter regulatory regions including transcriptional start site can be excised by XhoI-BbVII digestion. The complete LAT gene, with promoter, can be excised as a 6.0 kb XhoI fragment.

DETAILED DESCRIPTION OF THE INVENTION

The nervous system as a whole is divided into two systems, the central nervous system (CNS) and the peripheral nervous system (PNS). The CNS consists of the brain and spinal cord. The PNS consists of the sensory receptors which interact with the CNS via the afferent sensory nerves. The PNS also included motor effectors consisting of voluntary skeletal muscles, smooth muscles and glands. Efferent motor nerves extending from the CNS to these organs are also part of the PNS. The present invention provides compositions and methods for delivering genes to the CNS of a mammal.

The method of delivering genes to the central nervous system of a mammal constitutes somatic cell gene transfer suitable for a variety of neurological disorders such as Lesch-Nyhan syndrome (caused by HPRT deficiency) and mucopolysaccharidosis (MPS VII) (caused by β-glucuronidase deficiency) and other lysosomal storage diseases. Furthermore, this invention is useful for the delivery of a heterologous gene or selected DNA sequence that encodes a compound which alters any neurological function in a useful way, for example, such as the introduction of the tyrosine hydroxylase gene into Parkinson's disease patients which is believed to increase levels of DOPA. Another example is that the method can be used to code RNAs designed to block the expression of a gene in a mammal. The method is also useful for delivering genes that encode compounds that bind to receptors on neurons to alter functions of the cell, for example, blocking opiate receptors to modulate drug effects.

Neurotropic viral vector systems are utilized to deliver genes to the mammalian CNS. One vector comprises a recombinant virus containing the foreign gene to be expressed driven by a selected promoter. This viral vector preferably has deletions of viral certain genes which diminish the ability of the virus to form recurrent infections but do not affect the efficiency of formation of latent infections.

Using the method of the invention, it has been demonstrated for the first time that a foreign gene can be delivered to, and expressed over a long period of time (i.e., greater then 4 months) in the neurons of the CNS by peripheral infection with a neurotropic virus. It has also been demonstrated that it is possible to correct a deficiency in a biological function in cells of the central nervous system.

The Neurotropic Virus

As used herein, the phrase "neurotropic virus" refers to any virus capable of infecting the central nervous system (CNS) of a mammal Neurotropic viruses are well known to those of skill in the art. Examples of such viruses include, but are not limited to, HSV, CMV, HIV, JCV, BDV, HPV and pseudorabies virus. Conveniently, a neurotropic virus expected to be particularly suitable for use in this invention is the herpes simplex virus type 1 (HSV-1).

As used herein the phrase "neurotropic virus" is intended to include such portions of the neurotropic virus that are capable of being transmitted as a neurotropic virus genome to transfer the foreign gene into the CNS. An example of such a useful virus portion is an HSV-1 amplicon.

As used herein the term "amplicon" refers to a plasmid comprising sequences derived from the HSV origin of DNA replication and packaging signals capable of undergoing DNA replication. These amplicons form long linear concatemers which are generally packaged as 150 kb of DNA to form defective interfering particles in helper virus stocks as described in Spaete et al., "The herpes simplex virus amplicon: a new eucaryotic defective-virus cloning-amplifying vector,"*Cell* 30:295-304 (1982) and Deiss et al., "The herpes simplex amplicon: cleavage of concatemeric DNA is linked to packaging and involves the amplification of the terminally reiterated a sequence," *J. Virol.* 57:933-941 (1986a).

As used herein the term "promoter" refers to a DNA sequence which is used to drive transcription of the foreign gene during the latent infectious period of the neurotropic virus selected, including true promoters, tissue-specific or other enhancer sequences, locus control regions, and any other gene region used to control the expression of the foreign gene.

The term "gene" or "selected DNA sequence" as used herein is meant to include cDNA sequences, intronic sequences, and any other DNA sequences important to the expression of the foreign gene from the virus. This is meant to include any combination of sequences which are important to the function of the expressed product, such as fusion proteins or other modifications that may make the expressed product useful for modifying functions in the CNS. One of skill in the art can routinely select a gene or DNA sequence to be incorporated into the vector of the present invention based upon the compound to be expressed, the particular disease or condition to be treated, and the present disclosure.

By way of illustration, HSV-1 vectors are used below to further describe the present invention.

HSV-1 vector systems are utilized to deliver genes, by the method of this invention, to the mammalian CNS. One vector, in essence, is a recombinant virus containing the foreign gene to be expressed driven by a promoter as described below. This virus vector will preferably be deleted in certain genes to diminish the ability of the virus to form recurrent infections. However, these deletions will preferably not be of the type that affect the efficiency of formation of latent infections.

In addition to recombinant HSV-1 described above, HSV-1 offers an alternative approach for expression vectors in the form of amplicons (or defective interfering particles) as described above.

A productive lytic infection is not necessary for expression of genes cloned in neurotropic virus vector amplicons. All that is required is that recombinant amplicon must be able to bind to the cell and its DNA be delivered to the nucleus. This observation is consistent with the findings that the establishment of latency is a passive phenomenon which occurs in the absence of infectious virus production, in the absence of expression of immediate early and early genes, and in the absence of DNA replication. Steiner et al., "A herpes simplex virus type 1 mutant containing a non-transinducing Vmw65 protein establishes latent infection in mouse trigeminal ganglia in the absence of viral replication", *J Virol*, 64:1630-1638 (1990). By using genetically engineered mutants lacking in transactivating activity or thymidine kinase activity, it has become clear that the establishment of a latent infection, and the subsequent transcription of the LAT gene in HSV, can occur in the absence of viral transcription during the lytic cycle and DNA replication. For this reason, using HSV-1 amplicons provides a feasible method for transferring and targeting foreign genes to the CNS.

The construction of recombinant HSV-1 vectors for targeting genes of interest into the CNS can be achieved in several steps: selection and cloning of the appropriate upstream region of the gene containing promoter regulatory elements and the transcriptional start site; placement of genes of interest or cDNA downstream of the promoter; and cloning of the functionally active chimeric transcriptional unit into a neurotropic virus vector.

The Promoter

Useful promoters are capable of expressing the heterologous gene during the latent infectious state from the selected neurotropic virus. For example, the HSV-1 LAT promoter is a suitable promoter for use in this invention. Other promoters may be more suitable depending on, inter alia, the neurotropic virus, the heterologous gene and the desired levels of gene expression.

Figure 1:
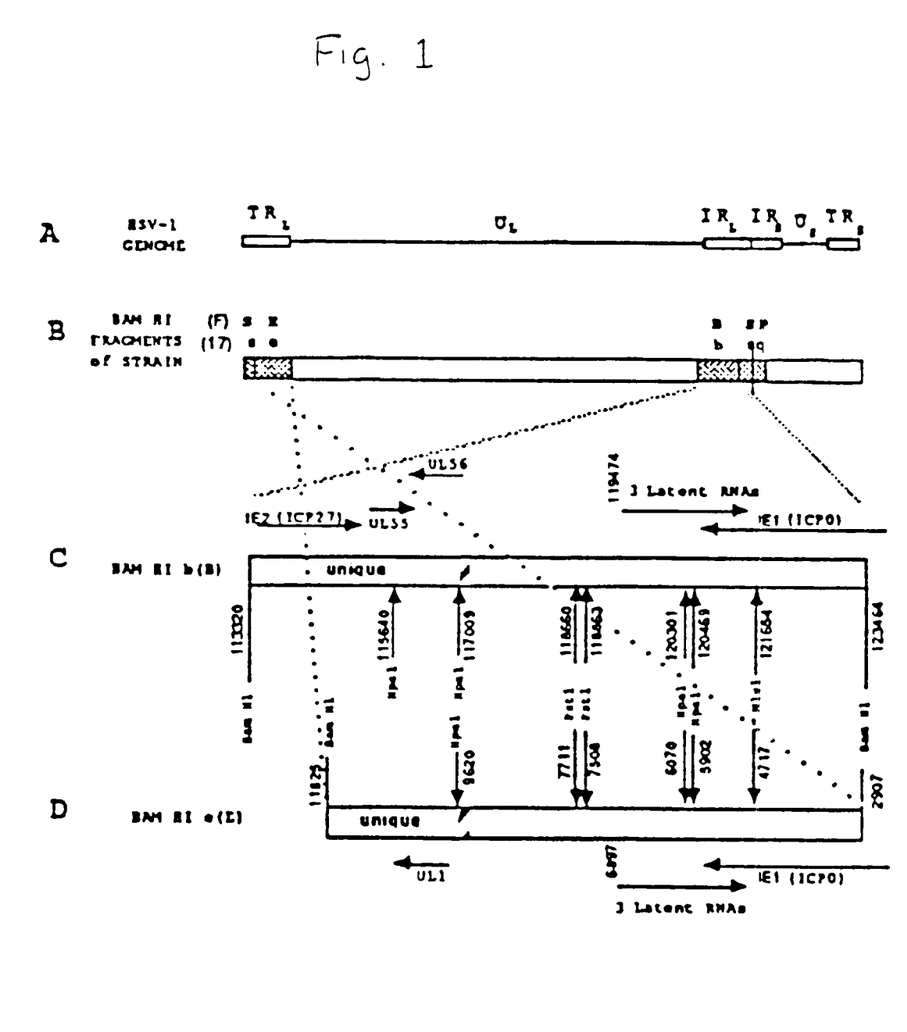

By way of illustration only, the LAT promoter of HSV-1 is described in detail herein. During latency, the HSV-1 genome resides in an episomal (non-integrated) form in the nucleus of neuronal cells. None of the genes expressed during the lytic infection are expressed during latency. However, there is expression from a viral promoter (the promoter of the latency associated transcript, LAT) which results in high levels of LAT RNA in neuronal cells. Thus, the LAT promoter is particularly useful for the expression of foreign genes in neuronal cells of the CNS. The disruption of the LAT gene when inserting the heterologous gene may enhance the method of the invention by reducing the virus' ability to reactivate and cause recurrent disease. It is believed that two copies of LAT genes are present in the long repeat region (BamHI B and E fragments) of HSV-1 DNA. In addition to sequences derived from the repeat region, both BamHI fragments B and E contain sequences from the unique region of the viral genome. This unique region in the BamHI B fragment codes for HSV-1 genes such as ICP27, UL55 and UL56 whereas the unique region of BamHI E codes for HSV-1 gene UL-1. The rest of the 6.6 kb region of the BamHI B and E fragment is derived from the long repeat region as shown in FIG. 1.

Figure 2:
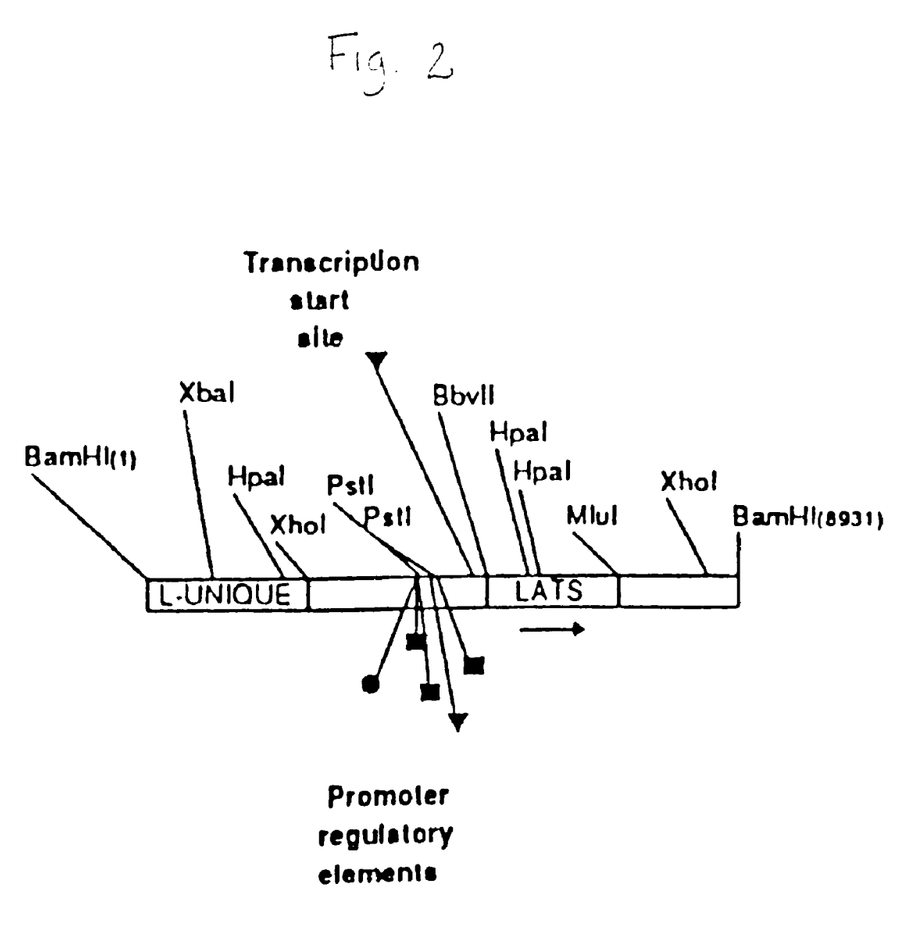

Three latency associated transcripts of size 2.0 kb, 1.50 kb, and 1.45 kb have been mapped to a 3 kb region (PstI-MluI) within the long repeat region [Spivack et al., "Detection of herpes simplex virus type 1 transcripts during a latent infection in mice," *J. Virol*. 61:3841-3847 (1987) and Stevens et al., "RNA complementary to a herpesvirus a gene mRNA is prominent in latently infected neurons," *Science* 235:1056-1969 (1987)]. The direction of transcription is opposite, and partially overlapping, the 3' end of the immediate early gene ICP0. The LAT transcriptional start site has been located at 4010 nucleotide position, in between SphI and BbVII sites, Wechsler et al., *J Virol*, 62:4051-58 (1988), shown in FIG. 2. From analysis of the sequence obtained by McGeoch et al., *Gen Virol*, 69:1531-74 (1988), and Wechsler et al., supra, (1988), a possible promoter has been proposed for the LAT. The TATA box for the promoter has been located at the –686 nucleotide position whereas a CAAT was located at 817. Three Spl binding sites have been detected at positions –886, –862, and –589. The combination of a TATA box, a CAAT box, and several GC boxes make this region an excellent candidate for a transcriptional promoter. Deletions in this region have resulted in virtually no detectable LATs either by in situ hybridization or Northern blot hybridization analysis [Steiner et al., "Herpes simplex virus type 1 latency-associated transcripts are not essential for latent infection," *EMBO* 8:505-511 (1989)]. Such a long distance (685 nucleotides) between a TATA box and the 5' end of the transcript make the LAT promoter unusual and may contribute to long term transcription in infected neurons.

An XhoI fragment of size 6.0 kb from within the repeat region of BamHI E and B fragments has been cloned into the XhoI site of pGEM7ZF. From this construct, a 2.744 kb fragment from XhoII to HpaI can be isolated and used as the LAT promoter (pSD102). This region would essentially contain the TATA, CAAT box, sp1 binding sites, and transcriptional start sites as proposed by Wechsler et al., supra, (1988).

Selection of Neurotropic Virus Vector Strains for Vector Construction

The selection of neurotropic virus vector strains for vector construction is not believed to be critical. The selection of strains will be governed by characteristics such as the particular areas of the CNS that are to be targeted for gene transfer. Safety of the virus for use in the methods of the invention will be governed for example, by levels deemed acceptable for the particular gene to be transferred, the severity of the disorder and the condition of the mammal. For instance, although both HIV and CMV are neurotropic, both are etiological agents of severe disease. In contrast, as almost all adults (more than 80%) have been latently infected with the HSV-1 virus, use of a HSV-1 vector does not introduce an additional viral challenge. Another advantage of the HSV-1 virus is that it has a wide host range and can infect humans, primates and mice.

For example, tk (thymidine kinase) deletion mutants, which are able to establish latent infections (as evidenced by expression LATs), but unable to reactivate in explant cultures, may be appropriate. These tk– mutants of HSV-1 replicate in cultured cells but fail to replicate in infected animals. Although they are unable to reactivate from latently infected ganglia, the presence of DNA and latency associated transcription has been shown [Tenser, et al., "Latency-associated transcript but not reactivatable virus is present in sensory ganglion neurons after inoculation of thymidine kinase-negative mutants of herpes simplex virus type 1," *J. Virol.* 63:2861-2865 (1989)]. Thus, for example, by using tk– mutants the heterologous gene can be delivered to the CNS without acute infection or reactivation.

The Heterologous Gene

It is believed that any heterologous gene or selected DNA sequence is suitable for delivery by the method of this invention. The heterologous gene or selected DNA sequence to be delivered can be made by a variety of methods including automated DNA synthesis.

Thus, the method of delivering genes to the central nervous system of a mammal of this invention constitutes somatic cell gene transfer suitable for a variety of neurological disorders such as Lesch-Nyhan syndrome (caused by HPRT deficiency) and mucopolysaccharidosis (MPS VII) (caused by β-glucuronidase deficiency) and other lysosomal storage diseases. Furthermore, this invention is useful for the delivery of a heterologous gene or selected DNA sequence that encodes a compound which alters any neurological function in a useful way, for example, such as the introduction of the tyrosine hydroxylase gene into Parkinson's disease patients which is believed to increase levels of DOPA. Another example is that the method can be used to code RNAs designed to block the expression of a gene in a mammal. The method is also useful for delivering genes that encode compounds that bind to receptors on neurons to alter functions of the cell, for example, blocking opiate receptors to modulate drug effects.

Cloning of Heterologous Sequences Downstream of the LAT Promoter, Chimeric Plasmid Construction The heterologous gene or selected DNA sequence for delivery to the CNS is cloned downstream of the LAT promoter by an y of the variety of methods known to those in the art. Generally, the gene is flanked on both ends with sequences obtained from the neurotropic virus to be used to promote homologous recombination.

Transfection and Identification of Chimeric Plasmids in Cultured Cells

To convert the chimeric plasmids into recombinant neurotropic virus vectors suitable for use in the invention, cells can be co-transfected with plasmid and neurotropic virus as described in Goldstein et al., "An ICP6::lacZ insertion mutagen is used to demonstrate that the UL52 gene of herpes simplex virus type 1 is required for virus growth and DNA synthesis," *J. Virol.* 62: 2970-2977 (1988). Usually a surplus (5 times more) of plasmid copies are used to ensure that there is a large pool of plasmid DNA for replication during virus infection. Alternatively, cells can be transfected with plasmid alone followed by infection of transfected cultures by virus to provide the packaging functions of helper virus vector.

Screening for recombinant viruses from the stock of post transfection progeny virus, prepared above, can be carried out by any method known to those in the art such as the method described by Villarreal et al., "Hybridization in situ of SV40 plaques: detection of recombinant SV40 virus carrying specific sequences of nonviral DNA," *Science* 196:183-185 (1977). Restriction endonuclease analysis of DNA extracted from recombinant viruses can be undertaken to confirm the specific recombination of plasmid sequences at the predetermined locations within the HSV-1 genome.

Additionally, construction of LAT-TK recombinants is believed to be a useful tool to simplify recombinant virus selection. Thymidine kinase enzyme has been shown to be essential for replication of virus in sensory neurons of infected mice although TK⁻ mutants have been shown to be able to replicate in ganglia at the site of inoculation. Leib et al., "A deletion mutant of the latency-associated transcript of herpes simplex virus type 1 reactivates from the latent state with reduced frequency," *J. Virol.* 63:2893-2900 (1989). In spite of their inability to replicate during acute infections or to reactivate from latent infection, TK⁻ mutants have been shown to establish latent infection and express the LAT gene (Leib et al., supra (1989)). Thymidine kinase gene has been used extensively as a marker to select recombinants since methodologies for selection in favor of both TK⁺ and TK⁻ are available. Generation of such a recombinant facilitates development of other recombinants because of the ease with which TK and TK⁺ recombinants can be enriched in the post transfection progeny viruses.

Delivery of Cloned Genes into Targeted Neurons of the CNS

The heterologous genes, genetically engineered into a neurotropic virus and under the control of a promoter as described, can be delivered to the CNS in any manner such that the virus is capable of entering the CNS of the mammal. Examples of such methods include peripheral inoculation, intranasal administration, intracranial injection and injection into the spinal fluid. Intranasal inoculation of HSV-1 and herpes virus allows for entry into the brain via the olfactory bulb. Peripheral inoculation into viscera can result in retrograde transport of virus into the CNS and hypothalamus. Migration of HSV-1 from infection in limbs to the CNS has been reported [Ugolini et al., "Transneuronal transfer of herpes virus from peripheral nerves to cortex and brainstem", *Science* 243:89-91 (1989)].

Those skilled in the art will recognize that the amount and frequency of viral vector administered will depend on a variety of parameters usually taken into consideration when dosing a mammal which parameters include but are not limited to the species of mammal, the age and condition of the mammal, the particular gene to be delivered and the reason for gene delivery. The viral vector can be added to a pharmaceutically acceptable carrier and systemically administered to the subject. Acceptable "pharmaceutical carriers" are well known to those skilled in the art and can include, but are not limited to any of the standard pharmaceutical carriers, such as phosphate buffered saline, water and emulsions, such as oil/water emulsions and various types of wetting agents.

As used herein, the term "administering" for in vivo purposes means providing the subject with an effective amount of the neurotropic viral vector containing the selected DNA sequence, such that a sufficient number of cells are transfected with the vector to produce a measurable amount of protein encoded by the selected DNA sequence. Administration can be effected continuously or intermittently throughout the course of treatment. Methods of determining the most effective means and dosage of administration are well known to those of skill in the art and will vary with the neurotropic viral vector used, the purpose of the therapy and the subject being treated.

Although not wishing to be bound by any particular theory as to a mechanism of action, it is believed that the method of the invention transfers a foreign gene along with the neurotropic virus genome into cells of the mammal at the site of inoculation. The recombinant virus replicates as an acute infections virus at the site of inoculation and infects peripheral neurons. In the neuron, the viral genome travels to the cell body in the ganglion, thence it is transferred by an as yet unknown process to connecting neurons of the CNS. For HSV and pseudorabies some of the retrograde transmission pathways have been partially mapped. Pseudorabies virus has been demonstrated to travel from visceral infection into the CNS [Card et al., "Neurotropic properties of pseudorabies virus: uptake and transneuronal passage in the rat central nervous system", *J. Neurosci.*, 10:1974-1994 (1990)], while HSV-1 has been shown to migrate from the peripheral to the central nervous system and was used as a tracer to delineate such transneuronal transmission pathways [Ugolini et al., "Transneuronal transfer of herpes virus from peripheral nerves to cortex and brainstem", *Science*, 243:89-91 (1989)].

The viral genome becomes latent in the CNS at which time only the promoter (suitable for use in the invention) is transcriptionally active. The foreign gene is expressed from the active promoter. The promoter drives transcription of the foreign gene and the normal biochemical machinery of the infected cell translates the foreign gene into the correct gene product. The gene product may act within the infected cell, or it may be released from the infected cell to act elsewhere.

Using the method of the invention, it has been demonstrated for the first time that a foreign gene can be delivered to, and expressed over a long period of time (i.e., greater then 4 months) in the neurons of the CNS by peripheral infection with a neurotropic virus. It has also been demonstrated by the method of the invention that it is possible to correct a deficiency in a biological function in cells of the central nervous system. Thus, recombinant neuroviruses, such as HSV-1, can be used to infect peripheral neurons through typical routes of viral infection including corneal scarification, intranasal exposure and foot-pad injection which lead to infection of neurons of the trigeminal ganglion, the olfactory system, and the cervical ganglion, respectively. The virus may also be delivered by injection through a spinal tap into the cerebrospinal fluid, or by infection into any tissue where the virus might gain access to the nervous system. Thus, the method of delivering genes to the CNS of a mammal of this invention constitutes gene therapy suitable for a variety of neurological dysfunctions.

The following examples are provided for illustrative purposes only and are not intended to limit the invention.

EXAMPLES

Materials & Methods

Animals:

Mice of the B6.C—H-2$^{bml}$/ByBir-GUSB$^{mps/mps}$ strain, which are homozygous for the genetic mutation in the GUSB gene, have been obtained from Jackson Laboratory, Bar Harbor Me.

The source of other materials used herein and not specifically identified are commercially available from a variety of biological supply houses.

Example 1 Chimeric Gene Constructs Based on the BstEII Site of the LAT Promoter

A 6.0 kb XhoI fragment located within the BamHI E fragment has previously been cloned into the XhoI site of pGEM 7zf plasmid. Except for about 200 bp which are derived from long unique region, the 6.0 kb XhoI fragment is derived from the repeat region of the HSV-1 genome and contains the LAT promoter and the LAT gene.

The XhoI fragment contains two PstI sites about 203 bp apart which contain most of the promoter regulatory elements such as the TATA box and 3 spl binding sites. It also contains 3 BstEII sites, located 420 bp, 1317 bp, 2294 bp down stream from the LAT TATA consensus sequence elements. The first two sites are exclusively located within the LAT coding region whereas the 3rd site is located within a LAT region which partially overlaps with an immediate early gene (ICPO). The strategy was to create a deletion within the LAT gene and replace it with foreign genes without creating any deletions within the ICPO gene since deletion mutants in the ICPO region are known to be inefficient in establishing latent infections (Leib et al., supra 1989). In order to achieve this, pXhoI-XhoI was double digested with SalI and XbaI restriction enzymes. The SalI site is located 2125 bp downstream of LAT promoter whereas the XbaI site is located within the polylinker region of the pGEM7zf sequences. A 7.0 kb pGEM7zf-HSV DNA fragment containing the XhoI-SalI (4.0 kb) insert sequences was gel isolated, the ends filled with nucleotides using the Klenow fragment of DNA polymerase, and the blunt ends were ligated. The resulting plasmid (pXhoI-SalI) contained two BstEII sites about 897 bp apart located 420 bp and 1317 bp downstream of LAT the promoter. These sites are ideally located for deletion and insertion of foreign genes. In order to achieve this, the plasmid XhoI-SalI was digested with BstEII to create a deletion of 897 bp (within the DNA encoding the 2 kb LAT RNA), and the pGEM7zf-HSV DNA fragment (6.0 kb) was gel isolated and ligated into this site. The resulting plasmid pΔBstEII has a unique BstEII site located 420 bp downstream of LAT promoter. The plasmid also has approximately 2.0 kb of flanking HSV DNA on one end (XhoI-BstEII) and approximately 800 bp (BstII-Sal) of flanking DNA sequence on the other end.

a. Engineering of a Construct with Multiple Cloning Sites

The next step was to introduce multiple cloning sites at the BstEII site so as to develop a generalized HSV-1 vector plasmid suitable for cloning genes of interest under the LAT promoter. This was achieved by cloning an ApaI to SacII DNA fragments from pLZRV-A into BstEII site of pΔBstEII. The 3.7 kb ApaI-SacII DNA fragment contains β-galactosidase with a SV40 poly A signal and many restriction sites derived from the Bluescript plasmid. The recombinant clones were selected by their ability to form blue colonies on X-gal containing plates. The plasmid preps were digested with BamHI to determine the orientation of the β-galactosidase gene, and a clone, with the β-galactosidase gene in the proper orientation with respect to the LAT promoter was selected. This clone (pβGAL-A) has unique SalI and XbaI sites which can be used to remove the β-galactosidase gene and replace it with other gene fragments containing SalI and XbaI ends. The plasmid can be linearized by XmnI digestion (a site within pGEM plasmid vector). Since the multiple cloning sites introduced into the LAT promoter plasmid are compatible with those of Bluescript, genes to be expressed from the LAT promoter such as GUSB, can be cloned into this modified Bluescript (ks) plasmid.

b. Engineering of a LAT GUSB Construct

The rat GUSB cDNA clone (a 2.1 kb EcoR1 DNA fragment) Wolfe et al., supra, (1990) was first cloned into Bluescript (ks) plasmid at the EcoR1 site. Recombinants were screened by KpnI digestion, which is asymmetrically located within the insert in order to determine the orientation of the GUSB gene with respect to restriction sites of the Bluescript (ks) plasmid. Clones with the proper orientation were selected and the GUSB gene was cut out as a SalI-XbaI fragment, gel isolated and force cloned into the SalI-XbaI sites of pβGAL-A described above. In order to do this, pβGAL-A was be digested with SalI and XbaI, and the resultant pGEM7zf-HSV fragment was isolated and ligated with the SalI-XbaI fragment of GUSB. To confirm insertion of GUSB sequences, plasmids were digested with SalI and XbaI to release the 2.4 kb GUSB fragment. In addition to this, other restriction digestions were performed to assure that the rat GUSB sequences were correctly oriented with respect to the LAT promoter.

Using this strategy, plasmid construct (pBRB) was produced wherein rat GUSB was placed under LAT promoter control at the BstEII site located 420 bp downstream of the TATA consensus sequences. The plasmid pBRB has a unique SphI site which was utilized to linearize the plasmid DNA. Linear plasmid DNA is more efficient than circularized plasmid DNA in cotransfection experiments with HSV-1 DNA in order to produce recombinant HSV-1 viruses. The flanking HSV-1 DNA sequences (2.0 kb on one side, 0.86 kb on the other) provided the homologous sequences essential for high efficiency recombination into the viral genome.

Example 2 Other Methods for Insertion of Foreign Genes Under Control of the LAT Promoter a. Chimeric Gene Constructs Based on the PpuMI Site of the LAT Gene In order to construct chimeric plasmids having a reporter gene at the PpumI site located at 724 downstream of the LAT promoter TATAA sequence, and 37 nucleotides downstream of the 5' end of LAT transcripts, a DNA fragment (EcoRV to SalI) within the long repeat region of the viral genome, having a unique PpuMI, site may be used. The plasmid Xhol-p-SalI is digested with EcoRV (site located in the insert) and EcoRI (site located within the polylinker). The plasmid DNA fragment of 5.2 kb containing both pGEM7zf and HSV sequences gel isolated, the ends filled with Klenow fragment of DNA polymerase, and ligated. The plasmid (pEcoSal) thus obtained has a EcoRV to SalI HSV DNA insert containing the LAT coding region. This plasmid is digested with PpuMI, end filled with Klenow, dephosphorylated with calf intestinal phosphatase, and ligated to reporter genes by following a strategy similar to that described above. The chimeric plasmid constructs provide about 860 bp of HSV-1 specific flanking sequence (EcoRV to PpuMI) on one side and about 1.4 kb (PpuMI to SalI) on the other side for homologous recombination.

b. Chimeric Gene Constructs Based on EagI (XmaIII) Site of LAT Promoter

A 200 bp PstI fragment containing most of the LAT promoter regulatory sequences and having a unique EagI (XmaIII) site 26 bp downstream of the LAT TATA box is isolated from the pEcoSal plasmid and cloned into pGEM3 plasmid. The orientation of the PstI fragment with respect to the polylinker is determined either by DNA sequencing or by restriction endonuclease analysis. The plasmid is digested with EagI and GUSB, or other reporter genes cloned at this site. The HSV-1 Pst fragment containing the GUSB sequences are removed from the pGEM3 plasmid and cloned into pEcoSal plasmid in order to provide efficient HSV-1 flanking sequences for homologous recombinants. The chimeric plasmid constructs are able to provide about 300 bp of HSV-1 specific flanking sequence (EcoRV to EagI) on one side and about 1.4 kb (EagI to SalI) on the other side for homologous recombination.

Example 3 Transfection

Viral DNA (500 ng of HSV-1 strain 17, equivalent to 200 plaque forming units (PFU) was mixed with 10-20 molar excess of linearized plasmid (pBRB described in paragraph 1b above), and precipitated by calcium phosphate onto cultured CV1 cells as described by Goldstein et al., supra (1988). Screening for recombinant viruses from the stock of post-transfection progeny virus was carried out by a method described by Villarreal et al., supra (1977). Briefly, total progeny virus from the cotransfected cultures was harvested, sonicated, serially diluted and plated onto CV1 cells. The infected cell cultures were maintained in medium containing 0.1% human gamma globulin to restrict the spread of virus. The medium was removed and the infected monolayers were overlaid with agarose. The solidified agarose was removed and saved for subsequent recovery of virus. The monolayers were transferred onto nitrocellulose and plaques and screened by hybridization with a probe specific for the GUSB gene. By analyzing autoradiographs, infectious recombinant viruses were identified and recovered from agarose, and plaque purified 3 times. The recombinants were GUSB positive and, since the recombinants had a deletion between BstEII sites they were negative with a BstEII fragment probe. Restriction endonuclease analysis of DNA extracted from recombinant viruses were used to confirm the specific recombination of plasmid sequences at the predetermined locations within the HSV-1 genome.

Example 4 Delivery of Cloned Genes into Targeted Neurons of the CNS

Adult MPS VII mice (8-12 weeks old) were anesthetized, their corneas were abraded with the tip of a 30 gauge hypodermic needle, and 20 μl of culture fluid containing $10^5$ to $10^6$ PFU of recombinant virus was put on each eye. The fluid was allowed to be absorbed and the animals recovered. At 7 to 9 days post-infection, the animals exhibited evidence of acute viral infection around the eyes, then recovered. These mice provide an animal model of mucopolysaccharidosis VII with well-defined genetics and pathophysiologies correlating to humans [Vogler et al., "A murine model of mucopolysaccharidosis VII. Gross and microscopic findings in beta-glucuronidase-deficient mice", Am. J. Pathol., 136:207-217 (1990)].

Example 5 Identification of GUSB Enzymatic Activity in the CNS

Figure 3:
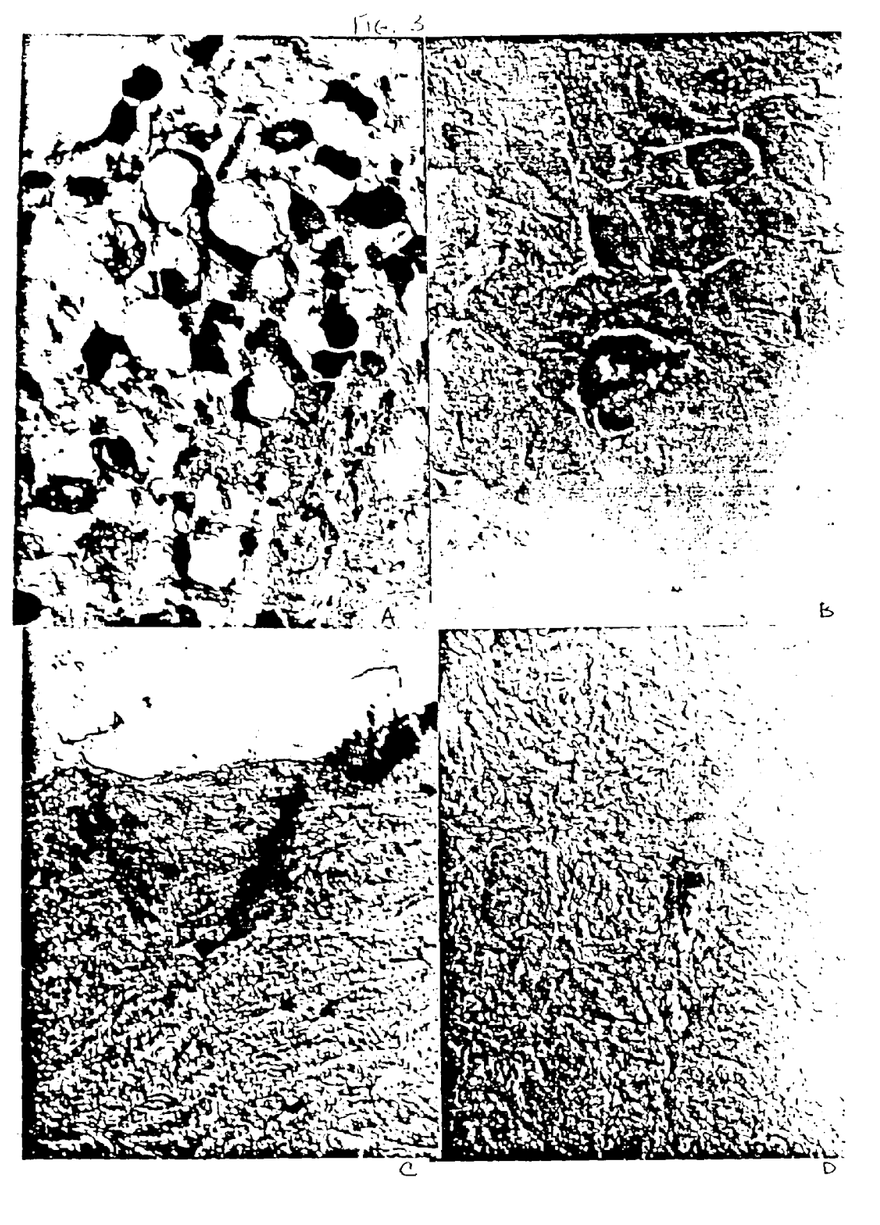
FIG. 3. Expression of β-glucuronidase (GUSB) enzymatic activity in cells of the trigeminal ganglion and brainstem of an MPS VII mouse infected with recombinant HSV-1 vector expressing the rat GUSB cDNA under control of the LAT promoter. A. Normal mouse trigeminal ganglion cells. B. Vector infected MPS VII mouse trigeminal ganglion cells showing a positive cell surrounded by negative cells. C. Vector infected MPS VII mouse trigeminal ganglion cells showing a group of positive cells surrounded by negative cells. D. Vector infected MPS VII mouse brainstem showing a positive cell surrounded by negative cells. METHOD: Cryostat sections of snap-frozen tissues were stained for GUSB activity (darker area) using the naphthol-AS-BI β-D-glucuronide substrate as previously described [Wolfe, et al., "Restoration of normal lysosomal function in mucopolysaccharidosis type VII cells by retroviral vector-mediated gene transfer,"*Proc. Natl. Acad. Sci.* 87:2877-2881 (1990)]. In over 100 tissue sections from uninfected GUSB-negative mice, a cell has never been shown to stain positive.

Animals were sacrificed between 14 and 126 days post-infection. The brain and the trigeminal ganglia were removed, immediately frozen in isopentane, cooled in liquid nitrogen for 25 seconds, transferred to liquid nitrogen temporarily, and stored at −70° C. The frozen tissues were cut into 10 micron sections and mounted on glass slides. The sections were assayed for the presence of GUSB enzymatic activity in situ using the method described in Wolfe et al., supra (1990) with the modification of carrying out the 37° C. incubation step for 16 hours instead of 4 hours. The reacted tissues were examine microscopically to identify cells expressing β-glucuronidase from the transferred gene. Positive cells stained red (dark as shown in FIG. 3).

Specific enzyme activity was detected in tissue sections up to 126 days (greater than 4 months). This is a significantly longer term of expression of a significant enzyme replacement target expressed in the CNS, than previously disclosed (about 3 weeks for the reporter gene β-globin in peripheral neurons) by Dobson et al., "Identification of the latency-associated transcript promoter by expression of rabbit β-globin mRNA in mouse sensory nerve ganglia latently infected with a recombinant herpes simplex virus", J Virology, vol. 63, No. 9, pp 3844-51 (1989). Such long term expression increase the therapeutic presence of ameliorative enzymes for a lysosomal storage disease and is a significant improvement in expensive and inefficient continuous infusion enzyme replacement therapy.

What is claimed is:

1. A method of stably expressing a selected DNA sequence in the central nervous system of a mammal comprising administering to peripheral neuron cells of a mammal a neurotropic viral vector which infects cells of the central nervous system of the mammal, said vector containing a selected DNA sequence operatively linked to a LAT promoter so that said selected DNA sequence is stably expressed for at least four months by infected central nervous system cells.

2. The method of claim 1 wherein the selected DNA sequence encodes β-glucuronidase.

3. The method of claim 1 wherein the selected DNA sequence encodes tyrosine hydroxylase.

4. The method of claim 1 wherein the viral vector comprises an HSV vector.

5. The method of claim 4 wherein the HSV vector comprises an HSV-1 strain.

6. The method of claim 5 wherein the HSV-1 strain comprises strain 17.

7. A method of stably expressing β-glucuronidase in the brain of a mammal comprising administering to peripheral neuron cells of a mammal a neurotropic viral vector which infects cells of the brain of the mammal, said vector being an HSV-1 vector containing a DNA sequence encoding β-glucuronidase operatively linked to a LAT promoter, so that the infected brain cells stably express β-glucuronidase.

8. The method of claim 7 wherein the HSV-1 vector comprises HSV-1 strain 17.

* * * * *